United States Patent [19]

Grasdepot et al.

[11] Patent Number: 5,920,391
[45] Date of Patent: Jul. 6, 1999

[54] TUNABLE FABRY-PEROT FILTER FOR DETERMINING GAS CONCENTRATION

[75] Inventors: François Grasdepot, Fontenay-aux-Roses; Jan Suski, Antony, both of France

[73] Assignee: Schlumberger Industries, S.A., Montrouge, France

[21] Appl. No.: 09/064,286

[22] Filed: Apr. 22, 1998

Related U.S. Application Data

[63] Continuation of application No. PCT/FR96/01675, Oct. 25, 1996.

[30] Foreign Application Priority Data

Oct. 27, 1995 [FR] France ................................. 95 12742

[51] Int. Cl.⁶ .................................................. G01B 9/02
[52] U.S. Cl. ........................... 356/352; 356/345; 359/291
[58] Field of Search ..................... 356/345, 352; 359/290, 291

[56] References Cited

U.S. PATENT DOCUMENTS

| | | | |
|---|---|---|---|
| 5,142,414 | 8/1992 | Koehler | 356/352 |
| 5,561,523 | 10/1996 | Blomberg et al. | 356/352 |
| 5,619,046 | 4/1997 | Engstrom et al. | 356/352 |
| 5,739,945 | 4/1998 | Tayebati | 356/352 |
| 5,835,216 | 11/1998 | Koskinen | 356/352 |

*Primary Examiner*—Robert Kim
*Attorney, Agent, or Firm*—Leonard W. Pojunas

[57] ABSTRACT

The invention provides a filter of the Fabry-Perot interferometer type for electromagnetic radiation having spectral density that is modified by a gas. The filter comprises a body which is transparent to said electromagnetic radiation, at least in its part through which the radiation passes. Said part comprises at least two portions possessing two facing surfaces that are mutually parallel and substantially plane. A "first" one of said portions is movable in a direction that is substantially perpendicular to the pair of facing surfaces. The filter further comprises: means for moving said facing surfaces between two extreme positions under the action of an electromagnetic field, and means for limiting adhesion between said surfaces in at least one of said positions in which said surfaces are at a distance apart which is small compared with the mean wavelength of the radiation passing through them.

20 Claims, 8 Drawing Sheets

TUNABLE FABRY-PEROT FILTER FOR DETERMINING GAS CONCENTRATION

This application is a continuation of PCT/FR96/01675 filed Oct. 25, 1996.

The invention relates to a filter for electromagnetic radiation having spectral density that is modified by a gas, the filter comprising a body which is transparent to said electro-magnetic radiation, at least in the part thereof through which the radiation passes, said part comprising at least two portions possessing two mutually parallel and substantially plane facing surfaces, separated from each other by a medium that does not present spectral interference with the gas, a "first" one of said portions being movable in a direction substantially perpendicular to the pair of facing surfaces.

BACKGROUND OF THE INVENTION

A filter possessing those characteristics is known from document EP 0 608 049.

In that document, electro-magnetic radiation, and more particularly optical radiation from a light source, passes through a cell containing a gas and has its spectral density modified by the presence of absorption lines in the gas.

The optical radiation modified in this way passes through an optical filter of the Fabry-Perot interferometer type constituted by a moving element disposed facing a fixed element. Together the two elements define a cavity between their respective facing surfaces.

The initial thickness of the cavity is selected so that the filter is tuned on the absorption band of the gas.

Downstream from the filter, a detector receives the radiation transmitted by the tuned filter and determines therefrom the energy which is representative of the gas concentration. This energy is a function of the wavelength of the gas.

In addition, a voltage is applied between the two facing surfaces in the cavity so as to displace the moving element and thus vary the thickness of the cavity, thereby having the effect of displacing the spectral transmission of the filter so that it is no longer tuned on the absorption band of the gas.

In this way, the detector detects radiation energy referred to as "reference" energy since it no longer depends on the wavelength of the gas.

Nevertheless, commonly-used light sources are rarely monochromatic and as a result they present a spectral distribution that covers a range of wavelengths on either side of the wavelength $\lambda_0$ which corresponds to an absorption line of the gas.

In addition, it happens very often that the gas whose concentration is to be 35 determined is not pure, but is mixed with other gases referred to as "parasitic" or "interfering" gases which possess interference lines for wavelengths lying within the spectral distribution of the source.

FIG. 1a shows the spectral distribution as output from the gas cell for radiation which has encountered an absorption line of a given gas for wavelength $\lambda_0$ and an absorption line of an interfering gas for wavelength $\lambda_1$.

FIG. 1b shows the spectral transmission of the filter used in document EP 0 608 049 when the filter is tuned on the wavelength $\lambda_0$ of the gas. In this figure, the spectral distribution of the radiation is shown in dashed lines.

FIG. 1c shows the energy measured (shaded area) by the detector when the filter is in the position shown in FIG. 1b.

In order to obtain a measured energy value which serves as a reference and which is thus independent of the wavelength $\lambda_0$ of the gas, it appears from the prior art document that by varying the thickness between the two facing elements of the filter, said filter is moved away from the absorption line of the gas.

However, as shown in FIG. 1b, it can happen that the new position of the filter corresponds to the wavelength of an interfering gas present in the mixture. Under such circumstances, the energy value measured by the detector (shaded area) that is supposed to act as a reference will be as shown in FIG. 1e.

If the energy values respectively measured by the detector in the cases shown in FIGS. 1c and 1e are written $S_0$ and $S_1$, and if the signal for determining gas concentration is written U, then:

$$U = S_0/S_1$$

More generally, this ratio can be expressed in the following form:

$$S_0/S_1 = (A+Bx)/(C+Dx)$$

where x represents the concentration of the gas.

To determine x, it suffices to solve the above equation. It can be seen that the accuracy with which x is determined is directly related to the accuracy with which the value U is obtained, giving:

$$\Delta U/U = \Delta S_0/S_0 + \Delta S_1/S_1$$

Unfortunately, when the reference value $S_1$ is as shown in FIG. 1e, the term $\Delta S_1/S_1$ is very large and this induces poor accuracy on the available signal U and thus on the determination of x.

OBJECTS AND SUMMARY OF THE INVENTION

The present invention seeks to remedy this drawback by proposing a filter which makes it possible greatly to reduce the influence of interfering gases in order to improve the accuracy with which the gas concentration is determined.

The present invention thus provides a filter for electromagnetic radiation having spectral density that is modified by a gas, the filter comprising a body which is transparent to said electromagnetic radiation, at least in the part thereof through which the radiation passes, said part comprising at least two portions possessing two mutually parallel and substantially plane facing surfaces, a "first" one of said portions being movable in a direction substantially perpendicular to the pair of facing surfaces, the filter further comprising:

means for moving said facing surfaces between two extreme positions under the action of an electromagnetic field; and means for limiting adhesion between said surfaces for at least one of said positions in which said surfaces are at a distance apart that is small compared with the mean wavelength of the radiation passing through them.

By bringing the facing surfaces into contact, the spectral transmission of the filter is moved away from the spectral distribution of the light source from which the electromagnetic radiation originates.

The term "contact" means bringing the facing surfaces to a distance apart that is small compared with the mean wavelength of the radiation passing through them, thus making it possible to keep down interference phenomena due to said surfaces. The term "contact" is used with this meaning in the specification below.

The effect of this displacement is to increase the transmission of the filter bringing it closer to a value of 1 over the entire spectral width of the radiation. As a result, if an interfering gas is present having a wavelength situated in the range of wavelengths delivered by the light source, its effect is so-to-speak "diluted" since the energy as measured is that of the radiation whose spectral density has been modified by the gases, attenuated by the transmission of the filter, which has a value close to 1. The reference value obtained in this way is more reliable than in the above-mentioned prior art.

It is possible to bring the facing surfaces into contact without fear of them sticking together and thus making the filter unusable by keeping down adhesion between these surfaces.

In addition, when the surfaces are in contact, the filter is in a mechanically stable position, thereby making it insensitive to mechanical vibration, which could have a large disturbing influence on measurement.

Each portion possesses a surface which is opposite the surface of said portion forming part of the pair of facing surfaces.

In order to obtain better contrast through the filter, and thus better resolution in subsequent determination of gas concentration, the opposite surfaces of the two portions are treated so as to transmit the electromagnetic radiation with practically no reflection.

In a second embodiment of the invention, the filter comprises a third body portion possessing a surface which is situated facing the surface of the first portion which is opposite from the surface of said first portion that forms a part of the first pair of facing surfaces, the facing surfaces of the first and third portions forming a second pair of mutually parallel and substantially plane facing surfaces.

In this embodiment, the filter also comprises means for moving the opposite surface of the first portion and the facing surface of the third portion between two extreme positions under the action of an electromagnetic field, and means for limiting adhesion between said surfaces for at least one of said positions.

In a third embodiment of the invention, the filter comprises a third body portion possessing a surface situated facing the surface of the second portion that is opposite from the surface of said second portion forming a part of the first pair of facing surfaces, the facing surfaces of the second and third portions forming a second pair of mutually parallel and substantially plane facing surfaces, the third portion being movable in a direction perpendicular to the facing surfaces.

In this embodiment, the filter comprises means for displacing the surface of the third portion and the opposite surface facing the second portion between two extreme positions under the action of an electromagnetic field, and means for limiting adhesion between said surfaces, in at least one of said positions.

When these means are activated together with the means for bringing the facing surfaces of the first and second portions into contact, the moving first and third portions are locked relative to the second body portion, thereby making it possible to obtain a reference position of the filter which is stable and insensitive to mechanical vibration.

According to other characteristics of the invention:

the means for displacing the surfaces comprise at least one source of voltage applied to said facing surfaces;

the surfaces are provided with electrodes which are connected to the terminals of the voltage source;

the material constituting the body portions is electrically conductive;

the sum of the distances between each pair of facing surfaces is substantially equal to $\lambda_0/2$, where $\lambda_0$ is the wavelength of the gas;

the means for limiting adhesion comprise mechanical abutments secured to one or both of the facing surfaces;

the means for limiting adhesion are formed by appropriate coatings deposited on one or both of the facing surfaces;

the means for limiting adhesion are formed by predetermined roughness imparted to one or both of the facing surfaces;

the surfaces are coated in an antireflection layer; and the electromagnetic radiation is preferably optical.

The invention also provides a device for determining a concentration of at least one gas, the device comprising:

a source of electromagnetic radiation which presents selective absorption relative to wavelengths of the gas;

a cell containing said gas and having the radiation passing therethrough;

a filter receiving the radiation whose spectral density has been modified by the gas;

a detector for detecting the filtered radiation to measure the energy of said radiation; and means for determining the concentration of the gas on the basis of two energy measurements, one of which serves as a reference value, wherein the filter possesses the above-described characteristics.

The invention also concerns a method of using a filter having the characteristics stated in claim 1, whereby at least one of the facing surfaces is moved to an extreme position in which said facing surfaces are spaced apart by a distance which is small relative to the mean wavelength of the radiation passing therethrough, after which said surface is moved away from said extreme position.

BRIEF DESCRIPTION OF THE DRAWINGS

Other characteristics and advantages will appear on reading the following description given by way of non-limiting example and made with reference to the accompanying drawings, in which:

FIG. 3b shows the energy as measured by the detector when the filter of the invention is in the position of FIG. 3a;

MORE DETAILED DESCRIPTION

Figure 2:
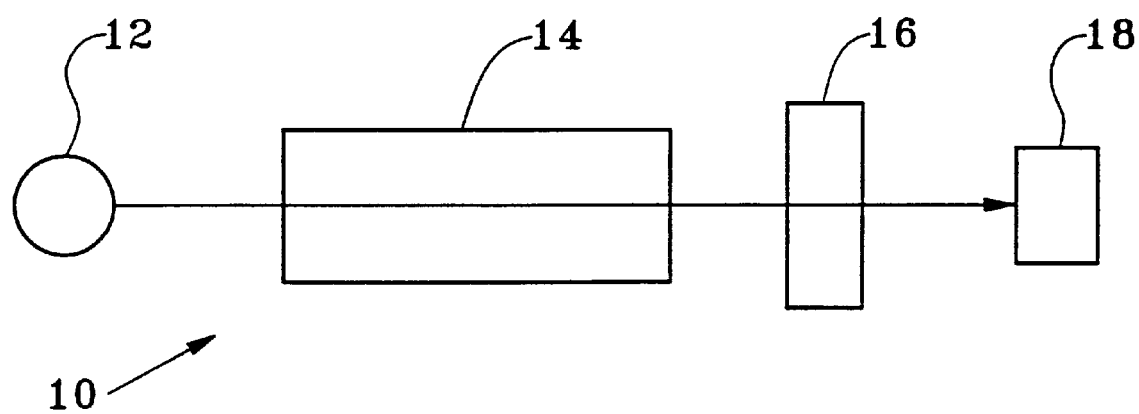
FIG. 2 is a view of a device for determining gas concentration and including a filter of the invention.

As shown in FIG. 2 under overall reference 10, a device for determining the concentration of a gas such as methane comprises a source 12 of electromagnetic radiation, e.g. a light source.

This source 12 may be an infrared lamp emitting radiation at a wavelength $\lambda_0 = 3.35$ μm. This wavelength corresponds to one of the absorption lines of the selected gas. The source has a spectral distribution in the wavelength range [2 μm; 4 μm].

The device 10 also has a cell 14 containing a gas at given concentration.

The radiation represented by the horizontal arrow in FIG. 2 passes through the cell 14 and is selectively absorbed by the gas.

At the outlet from the cell 14, the radiation presents spectral density that has been modified by the presence of absorption peaks due to it encountering the gas.

A bandpass type filter 16 receives this radiation and transmits it to a detector 18 which measures energy and which can be constituted, for example, by a bolometer.

The energy measured by the detector has an expression of the form:

$$S(\lambda) = \int_{\lambda_a}^{\lambda_b} I0(\lambda) Tg(\lambda) Tf(\lambda) d\lambda$$

where [$\lambda a$, $\lambda b$] is the spectrum width of the source 12, $I_0(\lambda)$ is the energy of the radiation emitted from the source 12, $Tg(\lambda)$ is the transmission coefficient due to the gas, and $Tf(\lambda)$ is the transmission coefficient of the filter.

Figure 3A:
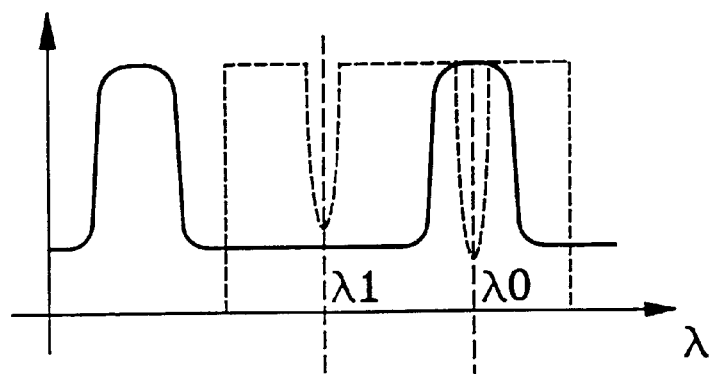
FIG. 3a shows the spectral transmission of the filter of the invention for a position tuned on the wavelength $\lambda_0$ of the gas.
Figure 3B:
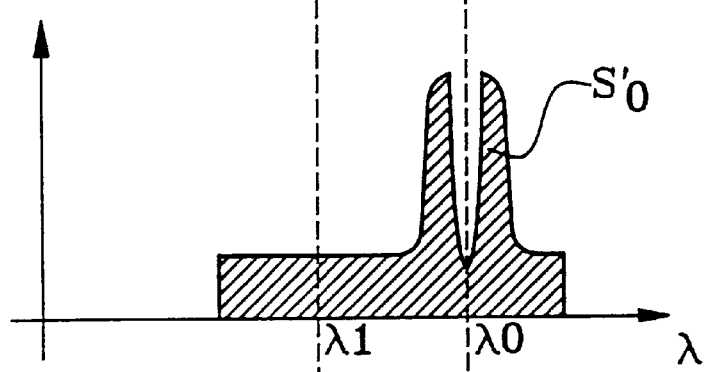
Figure 3C:
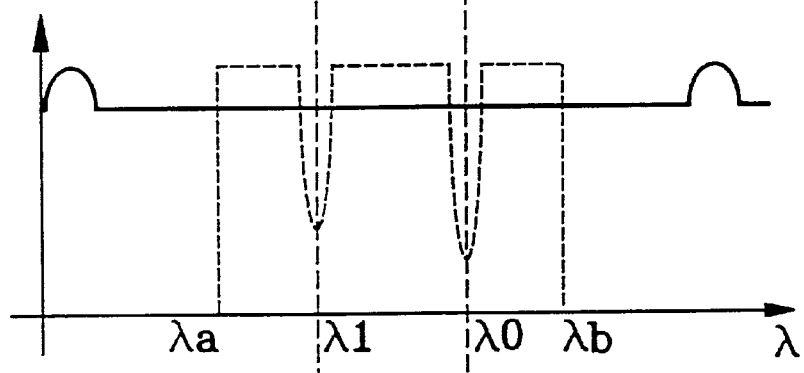
FIG. 3c shows the spectral transmission of the filter of the invention for a position that is offset relative to the wavelength $\lambda_0$ of the gas.
Figure 4:
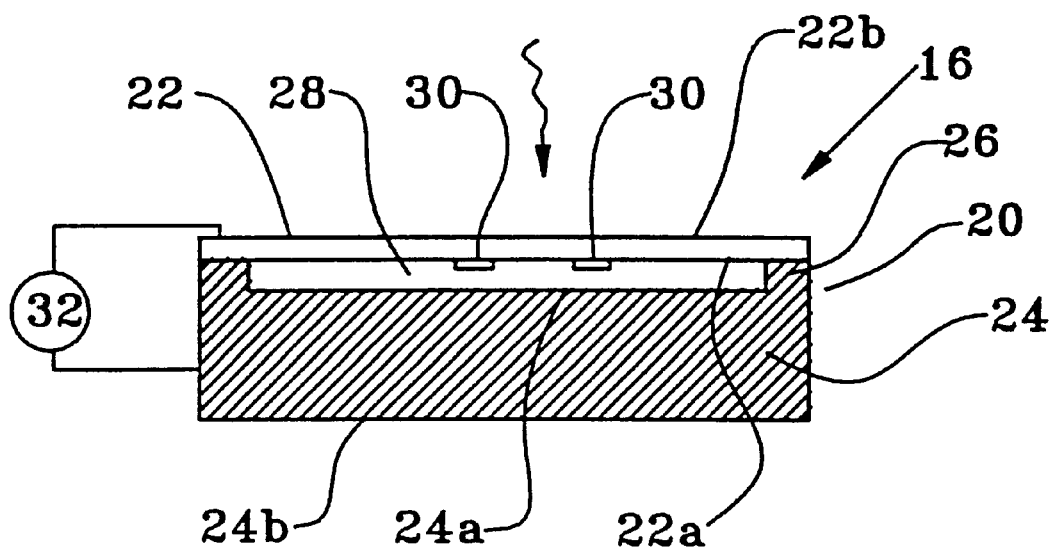
FIG. 4 is a section view through a filter constituting a first embodiment of the invention.

The filter 16 of the invention is of the Fabry-Perot interferometer type, as shown in FIG. 4, and it is used to perform a first measurement S'0 representative of the concentration of the gas (FIG. 3b). In this position, the filter is accurately tuned on the wavelength $\lambda_0$ of the gas as shown in FIG. 3a. Thereafter, the filter is used in a second position to take a second measurement S2 which serves as a reference. In this position, the filter is offset from the wavelength of the gas to outside the spectrum of the source 12, and the filter takes up a position in which its spectral transmission is as shown by the solid line in FIG. 3c.

In this figure, the dashed lines represent the spectral distribution of the light radiation coming from the gas cell and which has therefore encountered two absorption peaks, one corresponding to the wavelength $\lambda_0$ of the gas whose concentration is to be determined, and the other corresponding to the wavelength $\lambda_1$ of an interfering gas present in the gas.

It can thus be seen that the value of the spectral transmission of the filter between the fringes has been considerably increased by the invention compared with the filter described in document EP 0 608 049.

Figure 1A:
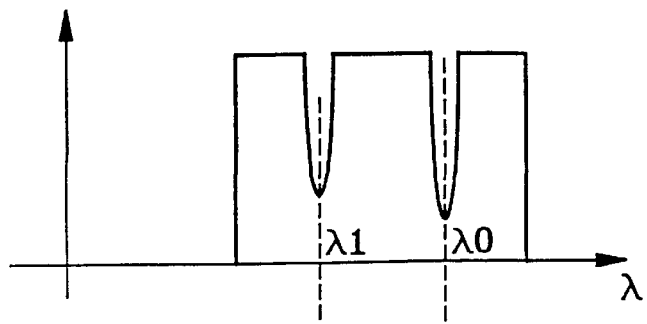
FIG. 1a shows the spectral distribution of radiation from the gas cell.
Figure 1B:
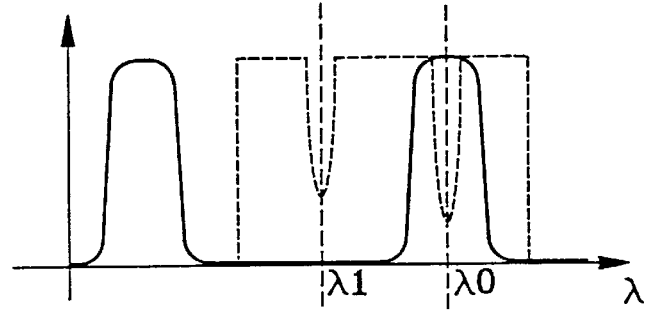
FIG. 1b shows the spectral transmission of the filter of document EP 0 608 049 when in a position that is tuned on the wavelength $\lambda_0$ of the gas.
Figure 1C:
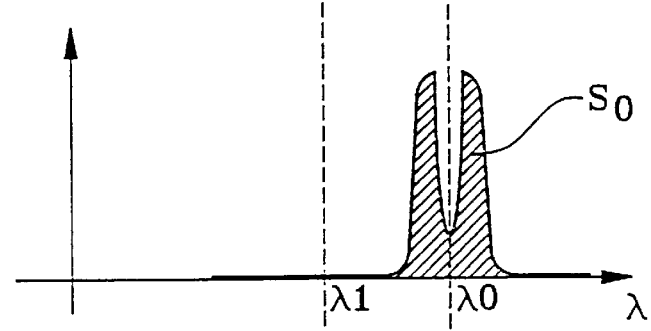
FIG. 1c shows the energy as measured by the detector when the filter is its position of FIG. 1b.
Figure 1D:
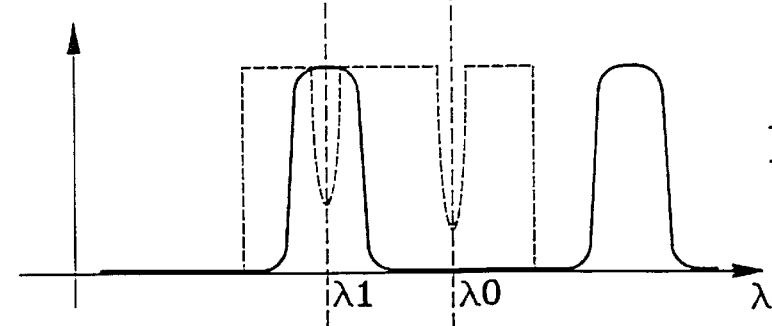
FIG. 1d shows the spectral transmission of the filter of document EP 0 608 049 in a position that is offset relative to the wavelength $\lambda_0$ of the gas but that is tuned on the wavelength $\lambda_1$ of an absorption line of a parasitic (interfering) gas.
Figure 1E:
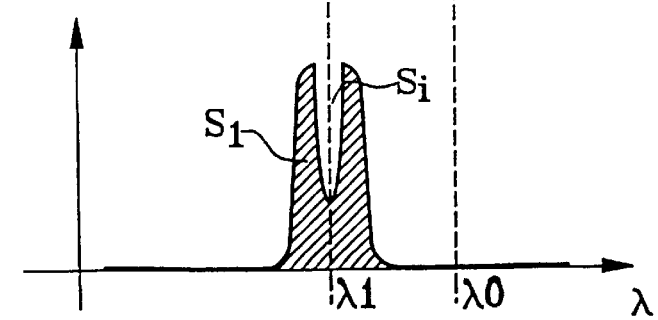
FIG. 1e shows the energy measured by the detector when the filter is in the position of FIG. 1d.
Figure 3D:
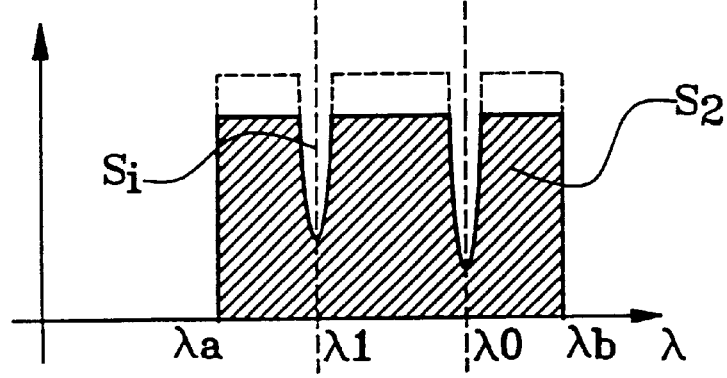
FIG. 3d shows the energy as measured by the detector when the filter is in the position of FIG. 3c.

Thus, when the energy $S_2$ (shaded area) as measured by the detector 18 in this "offset" position of the filter, which is to be used as a reference, is as shown in FIG. 3d, it can be seen that the ratio $S_i/S_2$ is much smaller than the ratio $S_i/S_1$ in the case of FIG. 1e prior art) where $S_i$ represents the energy due to the interfering gas having an absorption line of wavelength $\lambda_1$. This means that in the case of FIG. 3d the influence of the interfering gas is considerably reduced and as a result the gas concentration x obtained by solving the following equation:

$$S'_0/S_2 = (A+Bx)/(C+Dx)$$

is determined with much greater accuracy than in the prior art.

As shown in FIG. 4, the filter 16 of FIG. 2 is constituted by a body 20 which comprises a first portion formed by a membrane 22 that is substantially circular in shape. The body also has a second portion 24 forming a support that is of substantially cylindrical overall shape.

The membrane 22 is fixed on the support 24 by means of a peripheral rim 26 of said support 24.

The membrane 22 and the support 24 have two surfaces respectively 22a and 24a which face each other and which define between them a cavity 28 of thickness $e_0$.

These surfaces are substantially plane and mutually parallel.

For example, the cavity 28 may contain a medium which presents no spectral interference with the gas whose concentration is to be determined.

By way of example, the medium may be argon or some other inert gas, or even a liquid.

The cavity could also be evacuated.

The membrane 22 is movable relative to the support 24 in a direction which is perpendicular to the pair of facing surfaces 22a and 24a.

The light radiation having spectral distribution as shown in FIG. 3a is represented by a vertical arrow pointing towards the membrane 22. The body 20 is transparent to the selected light radiation, and is made of silicon, for example.

By way of example, such a filter can be obtained in the manner described in document EP 0 608 049 which describes the main steps of manufacture.

The surface 22a of the membrane is provided with mechanical abutments 30 which are obtained, for example, in the manner explained in the article entitled "Low drift integrated capacitive accelerometer with PLL servo technique" by Y. Matusmoto and M. Esashi, taken from "The 7th International Conference on Solid State Sensors and Actuators".

These abutments must be of a height that is small compared with the wavelength $\lambda_0$ of the gas when they are in the active zone of the filter, but it is also possible to place them outside said zone. For example, the abutments may have a height of $0.7'10^{-3}$ mm and can be made, for example, of a material such as SiON.

To make abutments in a material such as SiON or $SiO_2$ on the surface 22a which is made of silicon, for example, it is possible to proceed as follows, for example.

A layer of SiON or of $SiO_2$ is deposited on the surface 22a to a thickness of 2 μm, for example, by chemical or chemical vapor deposition (CVD) means, and then a layer of photosensitive resin (PPMA) and an optical photoetching mask is deposited, thus making it possible after exposure under ultraviolet light followed by conventional chemical development, to structure the resin so as to leave resin only in the locations where abutments are to be formed.

By protecting these zones and performing chemical etching by means of a solution of HF diluted in a ratio of 7:1 with water, the SiON or $SiO_2$ material is removed, except from the locations where it is desired to have the abutments.

Conventional cleaning makes it possible to remove the resin that remains in the locations of the future abutments.

Another layer of photosensitive resin (PPMA) is deposited on the surface together with an optical photoetching mask thus making it possible, after exposure and developing, to structure the resin over the abutment and leave resin only at other locations.

By protecting these zones and performing chemical etching using a solution of HF identical to the preceding solution, a sufficient thickness of the SiON or SiO2 material is removed from the abutment positions to obtain a final height of $0.7'10^{-3}$ mm.

The remaining resin is then removed by conventional cleaning.

The surfaces 22a and 24a are put into contact by the fact that the membrane 22 moves under the action of an electromagnetic field.

In the example shown in FIG. 4, the electrostatic field is created by a potential difference applied to the surfaces 22a and 24a by means of a voltage source 32 such as a battery.

Since silicon is electrically conductive, there is no need to provide electrodes that are transparent to the radiation on each of the faces. Nevertheless, it is necessary to insulate the membrane 22 electrically from the support 24, and that is not shown in the figures.

Figure 4A:
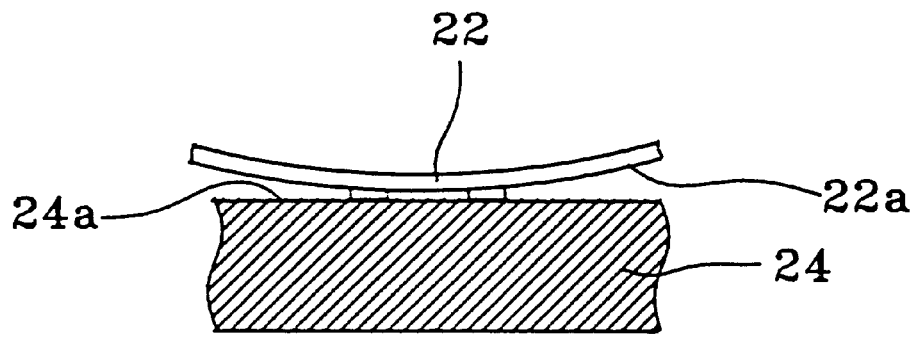
FIGS. 4a and 4c are fragmentary views of the FIG. 4 filter while in operation.

Under the action of a voltage, the surface 22a moves towards the surface 24a by the capacitive effect and it comes into contact therewith by means of the abutments as shown in FIG. 4a. In this position of the membrane 22, the filter is mechanically stable and can therefore be insensitive to mechanical vibration while it is in operation.

In addition, as mentioned above, in this position the filter is shifted relative to the wavelength $\lambda_0$ of the gas and a filter transmission spectrum is obtained as shown by the continuous line in FIG. 3c.

When positioned in this way, the filter is highly insensitive to interfering gases, thereby making it possible to obtain a reference energy reading $S_2$ (FIG. 3d) that is more reliable than in the prior art, and thus with greater accuracy concerning the concentration of the determined gas.

Because of the presence of the abutments 30, the surfaces 22a and 24a cannot adhere to each other on the molecular level which would cause said surfaces to "stick" together by creating chemical bonds between the various molecules of said surfaces.

It should be observed that in the filter of the invention no attempt is made to have spectral transmission that is as low as possible outside the fringes, as can be seen by comparing FIG. 3a with prior art FIG. 1b.

In Fabry-Perot interferometers, it is indeed known to seek fringes that are as narrow as possible and to seek a transmission value that is as small as possible between said fringes in order to avoid interfering gas wavelengths outside said fringes.

When the potential difference is removed, the membrane 22 can return to its initial position.

It is also possible to limit adhesion between the surfaces 22a and 24a by conferring predetermined roughness to one or the other or both of said surfaces, where the height of the relief of the roughness created in this way is less than the wavelength $\lambda_0$.

It is also possible to envisage modifying the surface(s) microscopically so as to prevent molecular bonds being created when they come into contact.

For example, this can be performed by ionically implanting nitrogen over a thickness of a few tens of nanometers using a quantity of ions that is of the order of $10^{15}$ ions/cm$^2$.

Figure 4B:
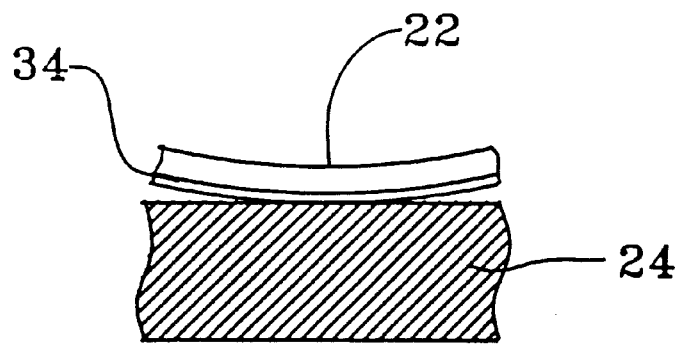
FIG. 4b is a fragmentary view of a variant embodiment of the filter shown in FIGS. 4 and 4a, shown while in operation.

It is also possible to coat the surfaces that are to come into contact with layers of suitable materials for the purpose of reducing adhesion, as shown by the variant of FIG. 4b. For example, a layer of thickness lying in the range 500 Å to 1000 Å of a material such as gold is suitable for this application.

In FIG. 4b, dimensions have deliberately been exaggerated so as to show the layer 34 of material. Such a layer can be deposited, for example, using the technique known as cathode sputtering, or by electrolytic deposition.

The surfaces can also be treated by a high level of arsenic doping.

It is also possible to envisage depositing n-alkyltricholosilane on the surfaces that are to come into contact by soaking them in a solution in which the molecules of n-alkyltricholosilane are dissolved in a solution of hexadecane at a concentration lying, for example, in the range $10^{-3}$ mol/l to $10^{-2}$ mol/l. Such a substance is sold, for example, by the Aldrich company.

When the membrane is in its initial position (thickness $e_0$), the energy $S'_0$ of the radiation transmitted by the filter is measured. The thickness e0 is designed so that the fringe of the filter is in the position which corresponds to the spectral transmission shown in FIG. 3a. This thickness is therefore selected to be equal to $\lambda_0/2$.

Figure 4C:
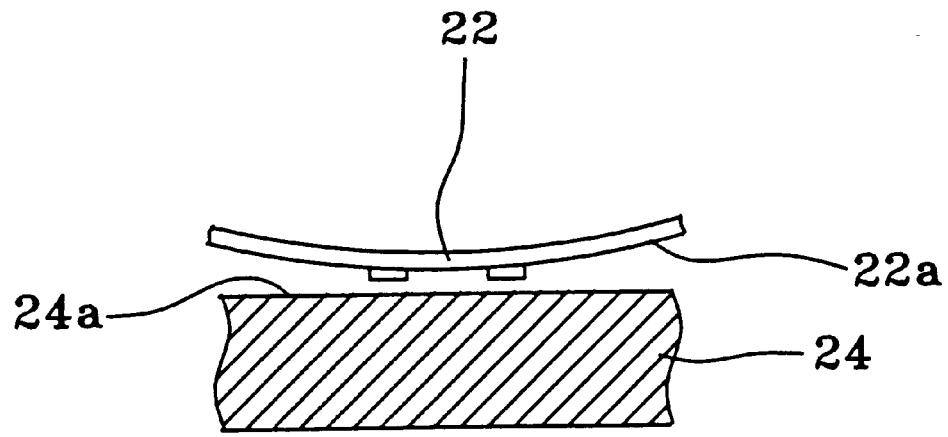

FIG. 4c shows one way in which the filter of the invention can be used, in which the voltage between the membrane 22 and the support 24 is adjusted to obtain a thickness that is smaller than $e_0$.

It is thus possible to take up a position that is accurately centered on an absorption line of some other gas, which makes it possible given the reliable value for the reference energy $S_2$ to determine the concentration of said other gas present in the mixture with accuracy that is better than in the prior art.

To obtain better resolution concerning gas concentration than that which is described with reference to FIGS. 4, 4a, 4b, and 4c, the surfaces 22b and 24b, respectively remote from the surfaces 22a and 24a are treated so as to enable them to transmit the light radiation with practically no reflection.

For this purpose, it is known to deposit an antireflection layer on each of the surfaces 22b and 24b, e.g. a layer of $SiO_2$ or of $Si_3N_4$. It is also possible to dope the silicon constituting the surface 22b of the membrane 22 and the surface 24b of the support 24 so as to match the refractive index of the material to that of the surrounding air.

An antireflection layer is made in conventional manner by depositing an optical thickness equal to $\lambda_0/4$ of a material whose refractive index is equal to the square root of the refractive index of silicon.

It should be observed that instead of setting up an electrostatic field to move the membrane, it is possible to set up a magnetic field by placing a coil on the support 24 and a magnet in the vicinity thereof on the surface 22a of the membrane.

The membrane may also be a piezoelectric element.

Under such circumstances, the filter may be manufactured, for example, in accordance with the teaching of the article "Silicon pressure sensors using a wafer-bonded sealed cavity process" by Lalitha Parameswaran, Andrew Mirza, Wendy K. Chan, and Martin A. Schmidt, taken from "The 8th International Conference on Solid State Sensors and Actuators, and Eurosensors IX, Stockholm, Sweden, Jun. 25–29, 1995, p. 582".

Although not shown in the figures, it is essential for the membrane and the support to be electrically isolated, e.g. by zones of insulated oxide.

Figure 4D:
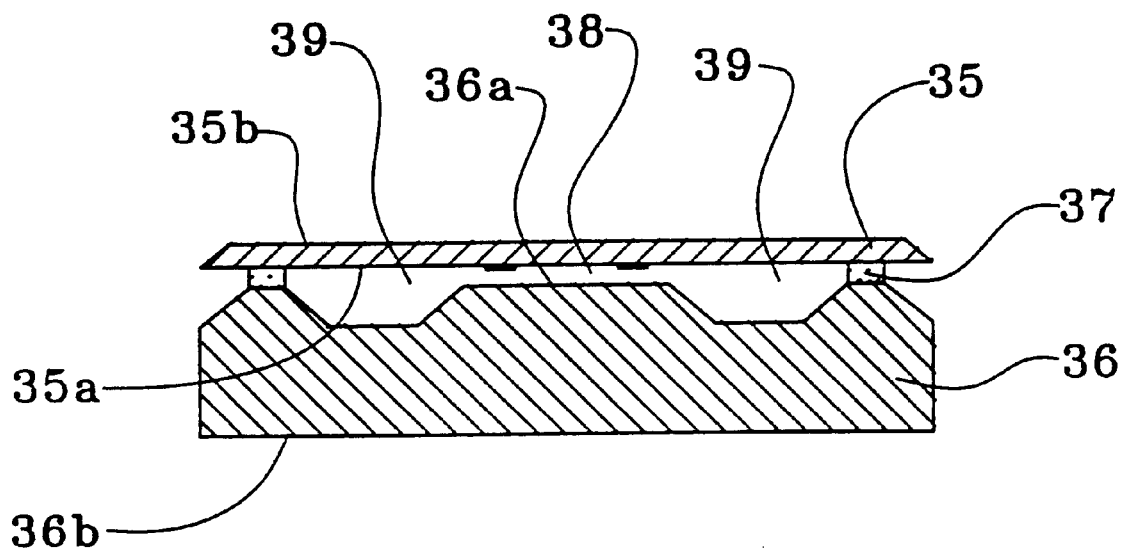
FIG. 4d is a section view of a filter constituting another variant embodiment of the embodiment shown in FIG. 4.

FIG. 4d shows a variant embodiment of the FIG. 4 filter. Such a filter is described by its structure in document FR 2 701 564 where the structure is that of a capacitive pressure sensor.

The filter shown in FIG. 4d comprises a body made up of two facing portions, a moving portion that forms a membrane 35 and a fixed portion that forms a support 36, which portions are electrically insulated from each other by a peripheral interconnecting frame 37. The respective facing surfaces 35a and 36a of the moving portion 35 and of the fixed portion 36 together define a central cavity 38 of substantially constant thickness communicating with a peripheral cavity 39.

By way of example, the cavities are filled with a gas that does not interfere spectrally with the gas to be analyzed, e.g. an inert gas such as argon.

The surface 35a is provided with abutments identical to those described with reference to FIG. 4. In addition, the outside surfaces 35b and 36b are provided with antireflection layers of $SiO_2$, for example.

Figure 5:
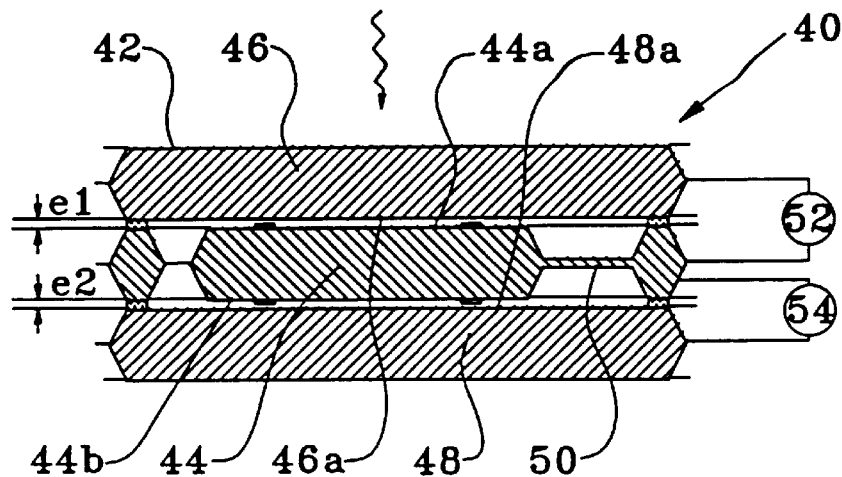
FIG. 5 is a section view of a filter constituting a second embodiment.
Figure 5A:
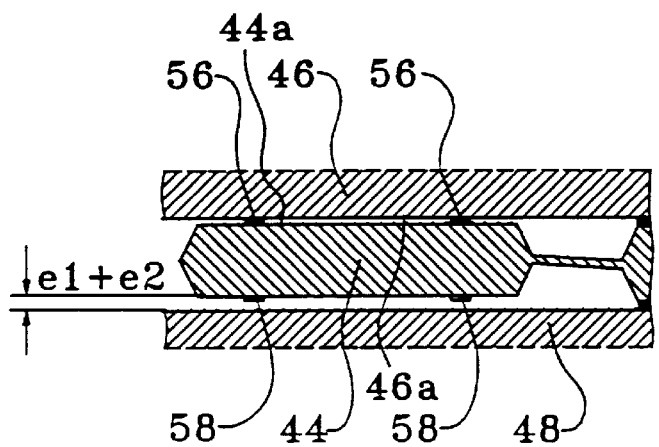
FIG. 5a is a fragmentary view of the FIG. 5 filter while in use.

A second embodiment of the invention is shown in FIGS. 5 and 5a.

The filter 40 of FIG. 5 can be made, for example, using the teaching of document FR 2 698 447.

In this embodiment, the filter 40 comprises a silicon body 42 constituted by a moving first portion 44 placed between two fixed portions 46 and 48.

Each fixed portion is in the form of a membrane that is electrically insulated from the moving portion.

The moving portion 44 is connected to the body 42 by an arm 50.

The filter constituted in this way has two pairs of mutually parallel and substantially plane facing surfaces, a first pair of surfaces 44a, 46a spaced apart by a thickness $e_1$ and a second pair of surfaces 44b, 48a spaced apart by a thickness $e_2$.

Each pair of facing surfaces forms a Fabry-Perot type interferometer.

By way of example, these surfaces are separated by a medium that does not interfere spectrally with the gas to be analyzed, e.g. argon or some other inert gas, or indeed a vacuum.

The first portion 44 can move in a direction perpendicular to the facing surfaces 44a, 46a, 44b, and 48a which corresponds to the direction in which the light radiation propagates, as symbolized by the vertical down arrow.

Two voltage sources 52 and 54 are provided to move the first portion 44 respectively towards the membrane 46 and towards the membrane 48, e.g. by using voltages of the order of several volts, which value can vary as a function of the stiffness of the first portion.

On its opposite surfaces 44a and 44b, the first portion 44 is provided with respective mechanical abutments 56 and 58 which make it possible to limit adhesion between the pairs of surfaces 44a and 46a and 44b and 48a. These abutments are obtained in the same manner as that described above.

As shown in FIG. 5a, the surfaces 44a and 46a come into contact via abutments 56, thus defining a stable mechanical position, with the reference position being given by the first portion disposed in the middle of the other two portions.

In the variant of the filter shown in FIGS. 5 and 5a, the facing surfaces 44b and 48a are treated so as to transmit the light radiation with hardly any reflection.

Figure 5B:
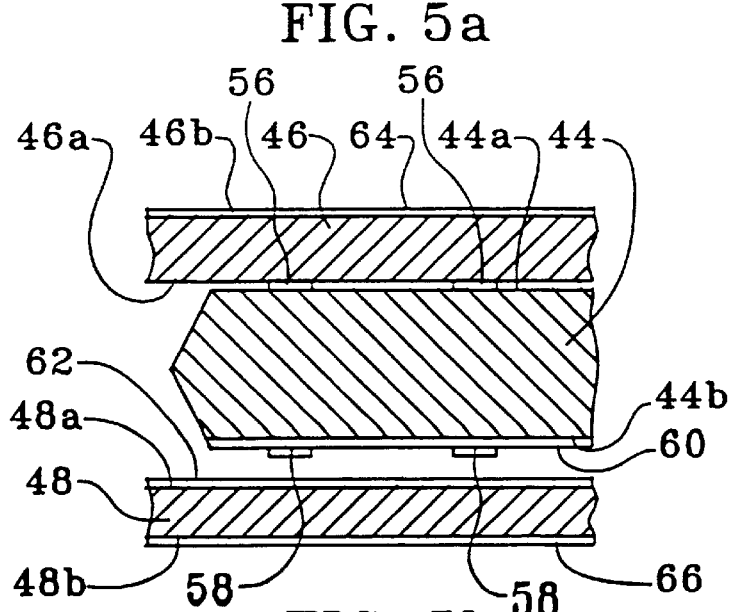
FIGS. 5b and 5c are fragmentary views of a variant embodiment of the FIG. 5 filter while in use.

Antireflection layers 60 and 62 of $SiO_2$ are deposited, for example, on the surfaces 44b and 48a respectively (FIG. 5b). Other treatments such as those mentioned above with reference to FIGS. 4 and 4a to 4c can also be envisaged.

Similarly, the surfaces 46b and 48b respectively opposite from the surfaces 46a and 48a are provided with antireflection layers 64 and 66.

When the first portion 44 occupies the position of FIG. 4b, the filter is in a stable "reference" position (FIG. 3c), and because of the antireflection layers 60, 62, 64, and 66, the filter provides essentially constant spectral transmission.

Figure 5C:
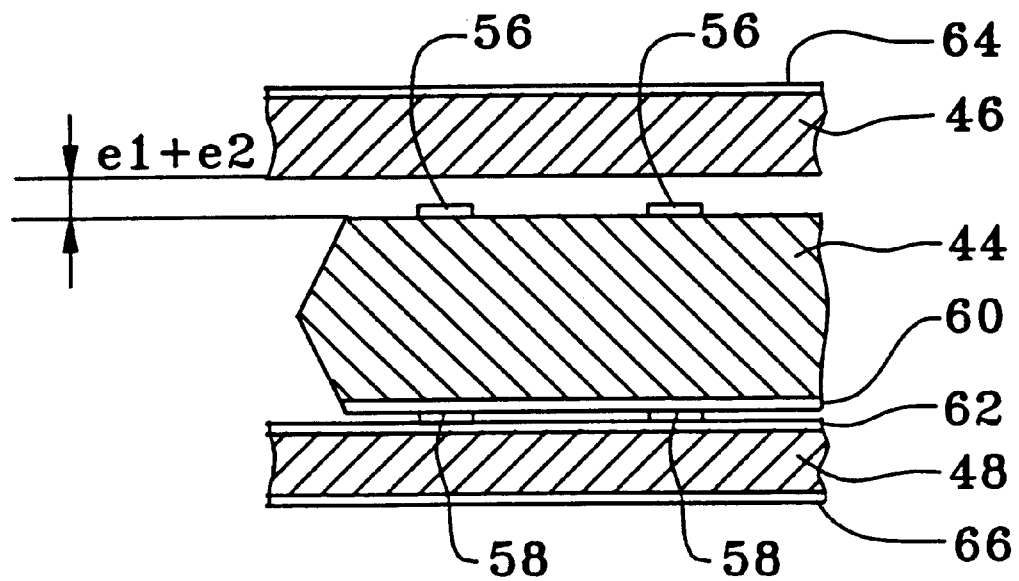

When the first portion 44 occupies the position of FIG. 5c, the filter is in a measurement position which is mechanically stable and no longer in a reference position.

By measuring the energy of the radiation received by the detector 18 in each of these positions, better contrast is obtained, and therefore better resolution concerning the concentration of the gas than is possible for the filter of FIGS. 5 and 5a.

Figure 5D:
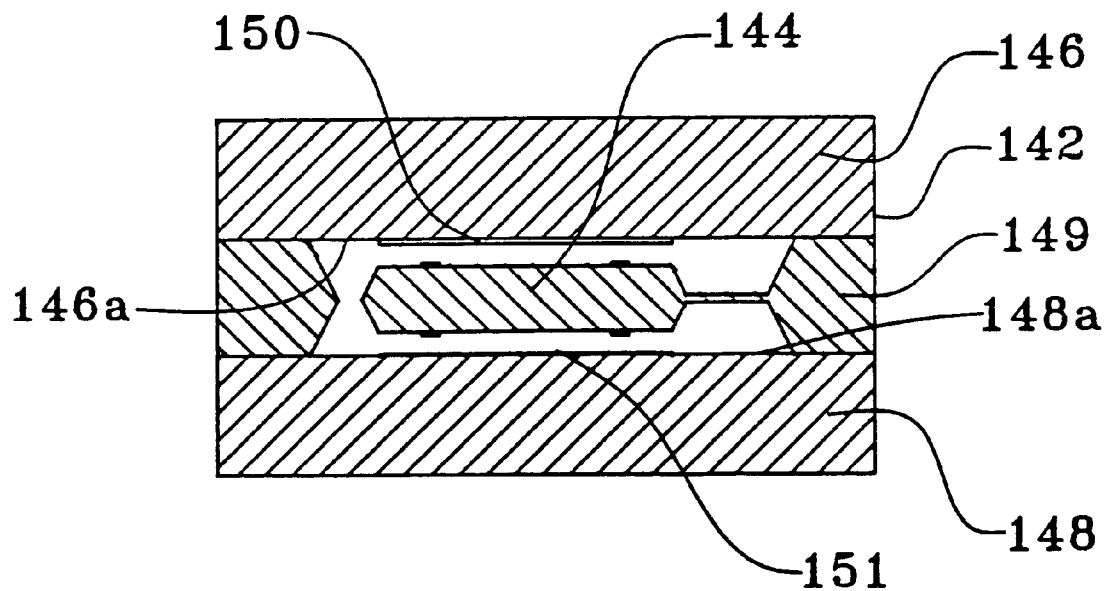
FIG. 5d is a section view of another variant embodiment of the FIG. 5 filter.

FIG. 5d shows a variant embodiment of the filter shown in FIGS. 5 and 5a.

The references including a number preceded by the digit 1 and the elements already described with reference to FIG. 5 are not described again below. The filter comprises a body 142 constituted by a moving portion 144 constituting a silicon moving electrode, and two fixed portions 146 and 148 of glass on either side of the moving electrode.

The two fixed portions 146 and 148 are spaced apart from each other by a spacer-formning piece of silicon 149 that acts as a support for the moving electrode 144.

The method of manufacturing such a structure is described in the article "Highly reliable silicon micromachined physical sensors in mass production" by Takao Sasayama, Seikoo Suzuki, Shigeki Tsuchitani, Akira Koide, Masayoshi Suzuki, Terumi Nakazawa, and Norio Ichikawa, taken from "The 8th International Conference on Solid-State Sensors and Actuators and Eurosensors IX, Stockholm, Sweden, Jun. 25 29, 1995, p. 688".

The moving electrode 144 is provided with abutments.

Each fixed portion 146, 148 is respectively provided on its face 146a, 148a with a semitransparent fixed electrode 150, 151 placed facing the corresponding face of the moving electrode 144.

Each of these fixed electrodes 150, 151 is connected to a voltage source (not shown).

Figure 6:
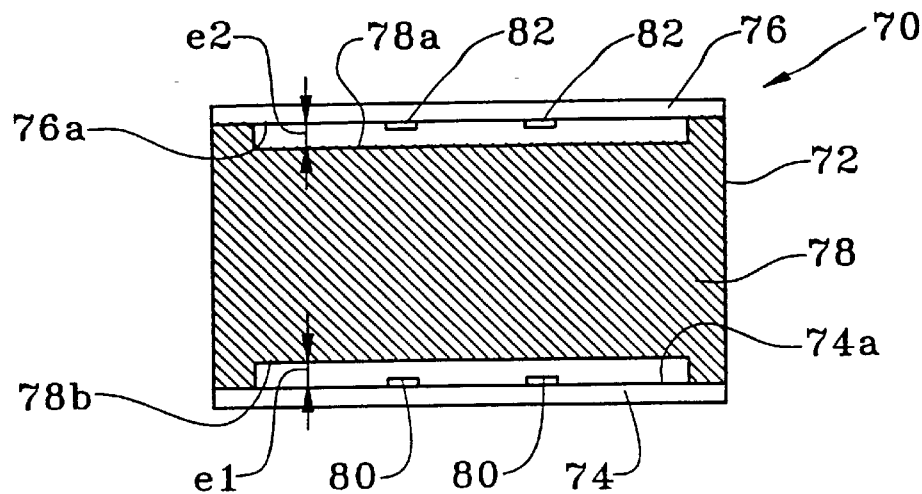
FIG. 6 is a view of a filter constituting a third embodiment of the invention.
Figure 6A:
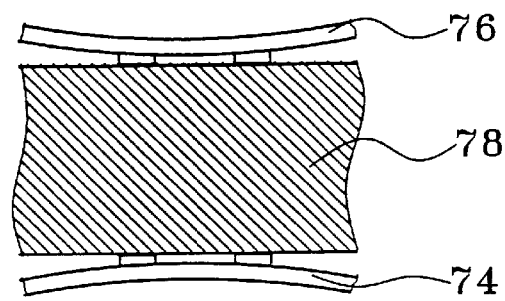
FIG. 6a is a fragmentary view of the FIG. 6 filter in operation.

In a third embodiment of the invention shown in FIGS. 6 and 6a, the filter 70 comprises a body 72 constituted by two moving portions 74 and 76 which are membranes mounted on either side of a central portion 78 forming a fixed support.

This embodiment is obtained by making the filter of FIG. 4 symmetrical about its horizontal base line.

A manufacturing process identical to that mentioned with reference to FIG. 4 and implemented on both faces of a wafer of silicon makes it possible to obtain the optical filter of FIG. 6.

The manufacturing process described in document FR 2 701 564 and implemented on both faces of a silicon wafer makes it possible to obtain the filter shown in FIG. 4 and a filter that is symmetrical about the horizontal base line of the support 36. Such a filter also corresponds to the third embodiment of the invention.

The filter has two pairs of facing surfaces 76a and 78a and 74a and 78b that are substantially plane and mutually parallel.

The surfaces 74a and 78b (or 76a and 78a) define between them a cavity which is filled with a gas such as argon, and they are spaced apart by a distance $e_1$ (or $e_2$).

Abutments 80 (or 82) are secured to the surface 74a (or 76a) of the membrane 74 (or 76) so as to limit adhesion between the surfaces when they come into contact via said abutments. These abutments could equally well be secured to the faces of the central portion 78.

In this position of the membranes, the thicknesses $e_1$ and $e_2$ are equal to $\lambda_0/4$ where $\lambda_0$ is the maximum absorption wavelength of the gas (FIG. 3a).

Although the membranes are free to move in any direction, when the filter is properly symmetrical, any mechanical vibrations imparted to the filter subject the membranes to the same displacement, and as a result the energy of the radiation transmitted by the filter in this position and as measured is influenced very little by such vibration.

It should be observed that the position of FIG. 6 is a position that is mechanically stable regardless of the thicknesses $e_1$ and $e_2$.

By applying a high voltage simultaneously to each pair of facing surfaces (the surfaces in each pair being electrically insulated from each other) the surfaces 74a and 76a of the membranes 74 and 76 are brought respectively into contact with the facing surfaces 78b and 78a of the support 78 via the abutments 80 and 82 (FIG. 6a).

Figure 6B:
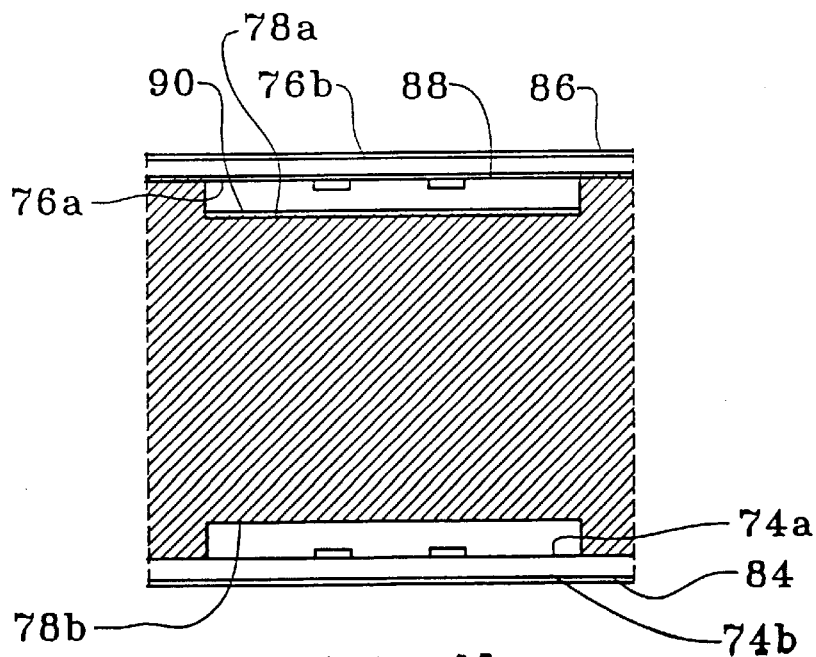
FIG. 6b is a view of a variant embodiment of the FIG. 6 filter in operation.

Voltage sources analogous to those shown in FIG. 5 are now shown in FIGS. 6, 6a, and 6b. FIG. 6a shows this perfectly stable reference position of the filter.

FIG. 6b shows a variant embodiment in which antireflection layers 84, 86, 88, and 90 have been deposited respectively on the surfaces 74b, 76b, 76a, and 78a so as to leave only one Fabry-Perot interferometer active in the filter: i.e. the interferometer constituted by the facing surfaces 74a and 78b.

It should be observed that the thickness between the facing surfaces 74a and 78b is equal to that $\lambda_0/2$.

This variant makes it possible to obtain contrast that is the same as when using the filter of FIGS. 6 and 6a, and thus to obtain the same resolution when determining gas concentration.

We claim:

1. A filter for electromagnetic radiation having spectral density that is modified by a gas, the filter comprising a body which is transparent to said electromagnetic radiation, at least in the part thereof through which the radiation passes, said part comprising at least two portions possessing two mutually parallel and substantially plane facing surfaces, a "first" one of said portions being movable in a direction substantially perpendicular to the pair of facing surfaces, the filter further comprising:

means for moving said facing surfaces between two extreme positions under the action of an electromagnetic field; and means for limiting adhesion between said surfaces for at least one of said positions in which said surfaces are at a distance apart that is small compared with the mean wavelength of the radiation passing through them.

2. A filter according to claim 1, in which each portion possesses a surface opposite from the surface of said portion that forms a part of the pair of facing surfaces, and said opposite surfaces of the two portions are treated in such a manner as to transmit the electromagnetic radiation with practically no reflection.

3. A filter according to claim 1, comprising a third body portion possessing a surface which is situated facing the surface of the first portion which is opposite from the surface of said first portion that forms a part of the first pair of facing surfaces, the facing surfaces of the first and third portions forming a second pair of mutually parallel and substantially plane facing surfaces.

4. A filter according to claim 3, comprising means for moving the opposite surface of the first portion and the facing surface of the third portion between two extreme positions under the action of an electromagnetic field, and means for limiting adhesion between said surfaces for at least one of said positions.

5. A filter according to claim 4, in which the facing surfaces of the first and third portions are treated so as to transmit electromagnetic radiation with practically no reflection.

6. A filter according to claim 5, in which each of the second and third portions possesses a respective surface opposite to its surface that forms a part of one of the pairs of facing surfaces, with said opposite surfaces of the second and third portions being treated in such a manner as to transmit electromagnetic radiation with practically no reflection.

7. A filter according to claim 1, comprising a third body portion possessing a surface situated facing the surface of the second portion that is opposite from the surface of said second portion forming a part of the first pair of facing surfaces, the facing surfaces of the second and third portions forming a second pair of mutually parallel and substantially plane facing surfaces, the third portion being movable in a direction perpendicular to the facing surfaces.

8. A filter according to claim 7, comprising means for displacing the surface of the third portion and the opposite surface facing the second portion between two extreme positions under the action of an electromagnetic field, and means for limiting adhesion between said surfaces, in at least one said positions.

9. A filter according to claim 7, in which the facing surfaces of the second and third portions are treated in such a manner as to transmit the electromagnetic radiation with practically no reflection.

10. A filter according to claim 7, in which each of the first and third portions possesses a respective surface that is opposite to its surface forming a part of a pair of facing surfaces, with said opposite surfaces of the first and third portions being treated in such a manner as to transmit the electromagnetic radiation with practically no reflection.

11. A filter according to claim 1, in which the means for displacing the surfaces comprise at least one source of voltage applied to said facing surfaces.

12. A filter according to claim 11, in which the surfaces are provided with electrodes which are connected to the terminals of the voltage source.

13. A filter according to claim 11, in which the material constituting the body portions is electrically conductive.

14. A filter according to claim 3, in which the sum of the distances between each pair of facing surfaces is substantially equal to $\lambda_0 2$, where $\lambda_0$ is the wavelength of the gas.

15. A filter according to claim 1, in which the means for limiting adhesion comprise mechanical abutments secured to one or both of the facing surfaces.

16. A filter according to claim 1, in which the means for limiting adhesion are formed by appropriate coatings deposited on one or both of the facing surfaces.

17. A filter according to claim 1, in which the means for limiting adhesion are formed by predetermined roughness imparted to one or both of the facing surfaces.

18. A filter according to claim 2, in which the surfaces are coated in an antireflection layer.

19. A filter according to claim 1, in which the electromagnetic radiation is preferably optical.

20. A device for determining a concentration of at least one gas, the device comprising:

a source of electromagnetic radiation which presents selective absorption relative to wavelengths of the gas;

a cell containing said gas and having the radiation passing therethrough;

a filter receiving the radiation whose spectral density has been modified by the gas;

a detector for detecting the filtered radiation to measure the energy of said radiation; and means for determining the concentration of the gas on the basis of two energy measurements, one of which serves as a reference value, wherein the filter is in accordance with claim 1.

* * * * *